United States Patent [19]
Celeste et al.

[11] Patent Number: 6,027,917
[45] Date of Patent: Feb. 22, 2000

[54] BONE MORPHOGENETIC PROTEIN (BMP)-17 AND BMP-18 COMPOSITIONS

[75] Inventors: Anthony J. Celeste, Hudson; Beth L. Murray, Arlington, both of Mass.

[73] Assignee: Genetics Institute, Inc., Cambridge, Mass.

[21] Appl. No.: 08/987,904

[22] Filed: Dec. 10, 1997

[51] Int. Cl.[7] ............................. C12N 1/21; C12N 5/10; C12N 15/12; C12N 15/63
[52] U.S. Cl. ..................... 435/69.1; 435/252.3; 435/325; 536/23.5; 536/23.51
[58] Field of Search ............................. 435/69.1, 252.3, 435/325; 536/23.5, 23.51

[56] References Cited

U.S. PATENT DOCUMENTS

| | | |
|---|---|---|
| 5,013,649 | 5/1991 | Wang et al. . |
| 5,071,834 | 12/1991 | Burton et al. . |
| 5,106,748 | 4/1992 | Wozney et al. . |
| 5,108,922 | 4/1992 | Wang et al. . |
| 5,116,738 | 5/1992 | Wang et al. . |
| 5,141,905 | 8/1992 | Rosen et al. . |
| 5,187,076 | 2/1993 | Wozney et al. . |
| 5,635,372 | 6/1997 | Celeste et al. . |
| 5,637,480 | 6/1997 | Celeste et al. . |
| 5,639,638 | 6/1997 | Wozney et al. . |
| 5,658,882 | 8/1997 | Celeste et al. . |

FOREIGN PATENT DOCUMENTS

| | | |
|---|---|---|
| WO 91/18098 | 11/1991 | WIPO . |
| WO 93/00432 | 1/1993 | WIPO . |
| WO 93/16099 | 8/1993 | WIPO . |
| WO 94/01557 | 1/1994 | WIPO . |
| WO 94/15949 | 7/1994 | WIPO . |
| WO 94/15965 | 7/1994 | WIPO . |
| WO 94/15966 | 7/1994 | WIPO . |
| WO 94/21681 | 9/1994 | WIPO . |
| WO 94/26892 | 11/1994 | WIPO . |
| WO 94/26893 | 11/1994 | WIPO . |
| WO 95/01801 | 1/1995 | WIPO . |
| WO 95/01802 | 1/1995 | WIPO . |
| WO 95/10539 | 4/1995 | WIPO . |
| WO 95/16035 | 6/1995 | WIPO . |
| WO 96/1845 | 1/1996 | WIPO . |
| WO 96/02559 | 2/1996 | WIPO . |
| WO 99/09198 | 2/1999 | WIPO . |

OTHER PUBLICATIONS

Zhou et al., Nature 361:543 (1993).
Ogawa et al, J. Biol. Chem. 267:14233–14237 (1992).
Murata et al., PNAS 85:2434–2438 (1988).
Yu et al., Nature 330:765–767 (1987).
Gentry et al., Mol. Cell. Biol. 8:4162 (1988).
Broxmeyer et al., PNAS USA 85:9052 (1988).
Eto et al., Biochem. Biophys. Res. Comm. 142:1095 (1987).
Matzuk et al., Nature 360:313 (1992).
Thies et al., J. Bone and Min. Res., 5:305 (1990).
Thies et al., Endocrinology 130:1318 (1992).
Derynck et al., Nature 316:701 (1985).
Jang et al., J. Virol., 63:1651–1660 (1989).
Dale et al., Cell, 90:257–269 (1997).
Meno et al., Nature 381:151:155 (1996).
Kothapalli et al. J. Clin. Invest. 99:2342–2350, May 1997.
Sambrook et al. Molecular Cloning, A Laboratory Manual. Cold Spring Harbor Laboratory Press, Cold Spring Harbor, NY, pp. 17.2–17.10, 1989.

*Primary Examiner*—Elizabeth C. Kemmerer
*Attorney, Agent, or Firm*—Steven R. Lazar; Barbara A. Gyure

[57] ABSTRACT

Purified BMP-17 and BMP-18 proteins and processes for producing them are disclosed. DNA molecules encoding the BMP-17 and BMP-18 proteins are also disclosed. The proteins may be used in the treatment of bone, cartilage, other connective tissue defects and disorders, including tendon, ligament and meniscus, in wound healing and related tissue repair, as well as for treatment of disorders and defects to tissues which include epidermis, nerve, muscle, including cardiac muscle, and other tissues and wounds, and organs such as liver, lung, epithelium, brain, spleen, cardiac, pancreas and kidney tissue. The proteins may also be useful for the induction of growth and/or differentiation of undifferentiated embryonic and stem cells.

17 Claims, No Drawings

BONE MORPHOGENETIC PROTEIN (BMP)-17 AND BMP-18 COMPOSITIONS

The present invention relates to a novel family of purified proteins designated as Bone Morphogenetic Proteins (BMP)-17 and BMP-18, related proteins, DNA encoding them, and processes for obtaining them. These proteins may be used to induce bone and/or cartilage or other connective tissue formation, and in wound healing and tissue repair. These proteins may also be used for augmenting the activity of other bone morphogenetic proteins.

BACKGROUND OF THE INVENTION

The search for the molecule or molecules responsible for the bone-, cartilage-, and other connective tissue-inductive activity present in bone and other tissue extracts has led to the discovery of a novel set of molecules called the Bone Morphogenetic Proteins (BMPs). The structures of several proteins, designated BMP-1 through BMP-16 have previously been elucidated. The unique inductive activities of these proteins, along with their presence in bone, suggests that they are important regulators of bone repair processes, and may be involved in the normal maintenance of bone tissue. There is a need to identify whether additional proteins, particularly human proteins, exist which play a role in these processes. The present invention relates to the identification of such a novel human protein, which the inventors have designated human BMP-17 and BMP-18.

Human BMP-17 and BMP-18 appear to be human homologs of a murine protein called Lefty. The nucleotide and amino acid sequences of murine Lefty are described in Zhou et al., *Nature*, 361:543–547 (1993). The murine Lefty gene has been described as being expressed in the mouse node during gastrulation. A related human protein, designated endometrial bleeding associated factor [EBAF] was published in Kothapelli et al., *J. Clin. Invest.*, 99:2342–2350 (1997).

SUMMARY OF THE INVENTION

As used herein, the term BMP-17 and BMP-18 proteins refer to the human BMP-17 and BMP-18 proteins, having the amino acid sequences specified in SEQUENCE (SEQ) ID NO:2 and SEQ ID NO: 4, as well as DNA sequences encoding the BMP-17 and BMP-18 proteins, such as the native human sequences shown in SEQ ID NO:1 and SEQ ID NO: 3. Also included are naturally occurring allelic sequences of SEQ ID NO:1 and 3, and equivalent degenerative codon sequences of the above.

The BMP-17 (SEQ ID NO: 1) and BMP-18 (SEQ ID NO: 3) DNA sequences and amino acid sequences (SEQ ID NO: 2 and 4, respectively) are set forth in the Sequence Listings. BMP-17 and BMP-18 proteins may be capable of inducing the formation of cartilage, bone, or other connective tissue, or combinations thereof. The cartilage and/or bone and/or other connective tissue formation activity in the rat bone formation assay described below. BMP-17 and BMP-18 proteins may be further characterized by the ability to demonstrate effects upon the growth and/or differentiation of embryonic cells and/or stem cells. Thus, the proteins or compositions of the present invention may also be useful for treating cell populations, such as embryonic cells or stem cell populations, to enhance or enrich the growth and/or differentiation of the cells. Alternatively, the proteins or compositions of the present invention may also be useful for maintenance of a cell population, including differentiated cell populations, for example, neuronal cells, epithelial cells, dendritic cells, chondrocytes, osteocytes, muscle cells or cells of other differentiated phenotypes.

Human BMP-17 proteins may be produced by culturing a cell transformed with a DNA sequence comprising nucleotide a DNA sequence encoding the mature BMP-17 polypeptide, comprising nucleotide #427 to nucleotide #1098 as shown in SEQ ID NO: 1, and recovering and purifying from the culture medium a protein characterized by the amino acid sequence comprising amino acids #1 to #224 as shown in SEQ ID NO:2 substantially free from other proteinaceous materials with which it is co-produced. For production in mammalian cells, the DNA sequence further comprises a DNA sequence encoding a suitable propeptide 5' to and linked in frame to the nucleotide sequence encoding the mature BMP-1 7-related polypeptide.

Human BMP-18 proteins may be produced by culturing a cell transformed with a DNA sequence comprising nucleotide a DNA sequence encoding the mature BMP-18 polypeptide, comprising nucleotide #406 to nucleotide #1098 as shown in SEQ ID NO: 3, and recovering and purifying from the culture medium a protein characterized by the amino acid sequence comprising amino acids #1 to #231 as shown in SEQ ID NO:4 substantially free from other proteinaceous materials with which it is co-produced. For production in mammalian cells, the DNA sequence further comprises a DNA sequence encoding a suitable propeptide 5' to and linked in frame to the nucleotide sequence encoding the mature BMP-18-related polypeptide.

The propeptide may be the native BMP-17 or BMP-18-related propeptide, or may be a propeptide from another protein of the TGF-β superfamily. Where the native BMP-17 and BMP-18 propeptide is used, human BMP-17 and BMP-18 may be produced by culturing a cell transformed with a DNA sequence comprising a DNA sequence encoding the full BMP-17 and BMP-18 polypeptide, comprising nucleotides #1 to #1098 as shown in SEQ ID NO: 1, or nucleotides #1 to # 1098 as shown in SEQ ID NO: 3, producing a protein characterized by the amino acid sequence comprising amino acids #–142 to #224 as shown in SEQ ID NO:2, of which amino acids #–142 to –1 comprise the native propeptide of human BMP-17; or #–135 to #231 of SEQ ID NO: 4 of which amino acids #–135 to –1 comprise the native propeptide of human BMP-18, and recovering and purifying from the culture medium a protein characterized by the amino acid sequence comprising amino acids #1 to #224 as shown in SEQ ID NO:2, or #1 to #231 of SEQ ID NO:4, respectively, substantially free from other proteinaceous materials with which it is co-produced.

Based in part upon the Von Heginje signal peptide prediction algorithm, approximately the first 17 to 23 amino acids of SEQ ID NO: 2 and 4 appear to be involved in signalling for the secretion of the mature peptide. Accordingly, in one embodiment of the invention, DNA encoding a signal peptide, such as the native BMP-17 or BMP-18 signal peptide, or another recognized signal peptide, may be linked directly to the sequence encoding the mature BMP-17 or BMP-18 peptide.

It is expected that other species, particularly human, have DNA sequences homologous to human BMP-17 and BMP-18 protein. The invention, therefore, includes methods for obtaining the DNA sequences encoding human BMP-17 and BMP-18 proteins, the DNA sequences obtained by those methods, and the human proteins encoded by those DNA sequences. This method entails utilizing the human BMP-17 and BMP-18 nucleotide sequences or portions thereof to design probes to screen libraries for the corresponding gene from other species or coding sequences or fragments thereof from using standard techniques. Thus, the present invention may include DNA sequences from other species, which are homologous to human BMP-17 and BMP-18 proteins and can be obtained using the human BMP-17 and/or BMP-18 sequences. The present invention may also include functional fragments of the human BMP-17 and BMP-18 proteins, and DNA sequences encoding such functional fragments, as well as functional fragments of other related proteins. The ability of such a fragment to function is determinable by assay of the protein in the biological assays described for the assay of the BMP-17 and BMP-18 proteins. DNA sequences encoding the complete mature human BMP-17 (SEQ ID NO: 1 and BMP-18 protein (SEQ ID NO:3) and the corresponding amino acid sequences (SEQ ID NO:2 and 4, respectively) are set forth herein. The BMP-17 and BMP-18 proteins of the present invention, such as human BMP-17 and BMP-18, may be produced by culturing a cell transformed with the correlating DNA sequence, such as the human BMP-17 and BMP-18 DNA sequence, and recovering and purifying protein, such as BMP-17 or BMP-18, from the culture medium. The purified expressed protein is substantially free from other proteinaceous materials with which it is co-produced, as well as from other contaminants. The recovered purified protein is contemplated to exhibit cartilage and/or bone and/or connective tissue formation activity. Thus, the proteins of the invention may be further characterized by the ability to demonstrate cartilage and/or bone and/or other connective tissue formation activity in the rat bone formation assay described below. BMP-17 and BMP-18 proteins may be further characterized by the ability to demonstrate effects upon the growth and/or differentiation of embryonic cells and/or stem cells. Thus, the proteins or compositions of the present invention may also be characterized by their ability to enhance or enrich the growth and/or differentiation of the cells.

Another aspect of the invention provides pharmaceutical compositions containing a therapeutically effective amount of human BMP-17 and/or BMP-18 protein, in a pharmaceutically acceptable vehicle or carrier. These compositions of the invention may be used in the formation of bone. These compositions may further be utilized for the formation of cartilage, or other connective tissue, including tendon, ligament, meniscus and other connective tissue, as well as combinations of the above, for example regeneration of the tendon-to-bone attachment apparatus. The compositions of the present invention, such as compositions of human BMP-17 and/or BMP-18, may also be used for wound healing and tissue repair. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in co-pending U.S. patent application Ser. No. 08/715,202. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of the above applications are hereby incorporated by reference.

The compositions of the invention may comprise, in addition to a BMP-17 and/or -18-related protein, other therapeutically useful agents including growth factors such as epidermal growth factor (EGF), fibroblast growth factor (FGF), transforming growth factor (TGF-α and TGF-β), activins, inhibins, and insulin-like growth factor (IGF). The compositions may also include an appropriate matrix for instance, for supporting the composition and providing a surface for bone and/or cartilage and/or other connective tissue growth. The matrix may provide slow release of the osteoinductive protein and/or the appropriate environment for presentation thereof.

The BMP-17 and/or BMP-18 containing compositions may be employed in methods for treating a number of bone and/or cartilage and/or other connective tissue defects, periodontal disease and healing of various types of tissues and wounds. The tissue and wounds which may be treated include epidermis, nerve, muscle, including cardiac muscle, and other tissues and wounds, and other organs such as liver, lung, epithelium, brain, spleen, cardiac, pancreas and kidney tissue. These methods, according to the invention, entail administering to a patient needing such bone and/or cartilage and/or other connective tissue formation, wound healing or tissue repair, an effective amount of a BMP-17 and/or BMP-18 protein. The BMP-17 and/or BMP-18 containing compositions may also be used to treat or prevent such conditions as osteoarthritis, osteoporosis, and other abnormalities of bone, cartilage, muscle, tendon, ligament or other connective tissue, organs such as liver, lung, epithelium, brain, spleen, cardiac, pancreas and kidney tissue, and other tissues. These methods may also entail the administration of a protein of the invention in conjunction with at least one other BMP protein as described above. In addition, these methods may also include the administration of a BMP-17 and/or BMP-18 protein with other growth factors including EGF, FGF, TGF-α, TGF-β, activin, inhibin and IGF.

Still a further aspect of the invention are DNA sequences coding for expression of a BMP-17 and/or BMP-18 protein. Such sequences include the sequence of nucleotides in a 5' to 3' direction illustrated in SEQ ID NO: 1 or SEQ ID NO: 3, DNA sequences which, but for the degeneracy of the genetic code, are identical to the DNA sequence SEQ ID NO: 1 or SEQ ID NO: 3, and encode the protein of SEQ ID NO: 2 or SEQ ID NO: 4. Further included in the present invention are DNA sequences which hybridize under stringent conditions with the DNA sequence of SEQ ID NO: 1 or SEQ ID NO: 3 and encode a protein having the ability to induce formation of cartilage, bone and/or other connective tissue, organs such as liver, lung, epithelium, brain, spleen, cardiac, pancreas and kidney tissue, or other activities disclosed for BMP-17 and BMP-18. Preferred DNA sequences include those which hybridize under stringent conditions [For example, see conditions described in Maniatis et al, *Molecular Cloning* (*A Laboratory Manual*), Cold Spring Harbor Laboratory (1982), pages 387 to 389]. It is generally preferred that such DNA sequences encode a polypeptide which is at least about 80% homologous, and more preferably at least about 90% homologous, to the conserved C-terminal cysteine structure of the amino acid sequence shown in SEQ ID NO:2 or SEQ ID NO: 4. Finally, allelic or other variations of the sequences of SEQ ID NO: 1 or SEQ ID NO: 3, whether or not such nucleotide changes result in changes in the peptide sequence, where the peptide sequence retains one or more BMP-17 and/or BMP-18 activity, are also included in the present invention. The present invention also includes fragments of the DNA sequence of BMP-17 and/or BMP-18 shown in SEQ ID NO: 1 or SEQ ID NO: 3 which encode a polypeptide which retains the activity of BMP-17 and/or BMP-18 protein.

The DNA sequences of the present invention are useful, for example, as probes for the detection of mRNA encoding BMP-17 and/or BMP-18 in a given cell population. Thus, the present invention includes methods of detecting or diagnosing genetic disorders involving the BMP-17 and/or BMP-18 gene, or disorders involving cellular, organ or tissue disorders in which BMP-17 and/or BMP-18 is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a BMP-17 and/or BMP-18 protein of the invention in which a cell line transformed with a DNA sequence encoding a BMP-17 and/or BMP-18 protein in operative association with an expression control sequence therefor, is cultured in a suitable culture medium and a BMP-17 and/or BMP-18-related protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Still a further aspect of the invention are BMP-17 and/or BMP-18 proteins or polypeptides. Such polypeptides are characterized by having an amino acid sequence including the sequence illustrated in SEQ ID NO: 2 or SEQ ID NO: 4, variants of the amino acid sequence of SEQ ID NO: 2 or SEQ ID NO: 4, including naturally occurring allelic variants, and other variants in which the protein retains the ability to induce the formation of cartilage and/or bone and/or other connective tissue, or other organs such as liver, lung, epithelium, brain, spleen, cardiac, pancreas and kidney tissue, or other activity characteristic of BMP-17 and/or BMP-18. Preferred polypeptides include a polypeptide which is at least about 80% homologous, and more preferably at least about 90% homologous, to the mature human BMP-17 and/or BMP-18 amino acid sequence shown in SEQ ID NO:2 or SEQ ID NO: 4. Finally, allelic or other variations of the sequences of SEQ ID NO: 2 or SEQ ID NO: 4, whether such amino acid changes are induced by mutagenesis, chemical alteration, or by alteration of DNA sequence used to produce the polypeptide, where the peptide sequence still has BMP-17 and/or BMP-18 activity, are also included in the present invention. The present invention also includes fragments of the amino acid sequence of BMP-17 and/or BMP-18 shown in SEQ ID NO: 2 or SEQ ID NO: 4 which retain the activity of BMP-17 and/or BMP-18 protein.

The purified proteins of the present inventions may be used to generate antibodies, either monoclonal or polyclonal, to human BMP-17 and/or BMP-18 and/or other BMP-17 and/or BMP-18-related proteins, using methods that are known in the art of antibody production. Thus, the present invention also includes antibodies to human BMP-17 and/or BMP-18 and/or other related proteins. The antibodies may be useful for purification of BMP-17 and/or BMP-18 and/or other BMP-17 and/or BMP-18 related proteins, or for inhibiting or preventing the effects of BMP-17 and/or BMP-18 related proteins. The BMP-17 and/or BMP-18 protein and related proteins may be useful for inducing the growth and/or differentiation of embryonic cells and/or stem cells. Thus, the proteins or compositions of the present invention may also be useful for treating relatively undifferentiated cell populations, such as embryonic cells or stem cell populations, to enhance or enrich the growth and/or differentiation of the cells. The treated cell populations may be useful for implantation and for gene therapy applications.

Description of the Sequences

SEQ ID NO:1 is a nucleotide sequence containing nucleotide sequence encoding the entire mature human BMP-17 polypeptide.

SEQ ID NO:2 is a amino acid sequence containing the mature human BMP-17 polypeptide sequence.

SEQ ID NO: 3 is a nucleotide sequence containing nucleotide sequence encoding the entire mature human BMP-18 polypeptide.

SEQ ID NO: 4 is a amino acid sequence containing the mature human BMP-17 polypeptide sequence.

DETAILED DESCRIPTION OF THE INVENTION

The human BMP-17 and BMP-18 sequences of the present invention may be obtained using the whole or fragments of the murine Leftv DNA sequence, or a partial human BMP-17 or BMP-18 sequence, as a probe. Thus, the human BMP-17 and BMP-18 DNA sequence comprise the DNA sequence of nucleotides #1 to #1098 of SEQ ID NO: 1 or #1 to #1098 of SEQ ID NO:3. The human BMP-17 and BMP-18 proteins comprise the sequences of amino acids #−142 to #224 of SEQ ID NO: 2, or #−135 to #231 of SEQ ID NO: 4, respectively. The mature human BMP-17 and BMP-18 proteins are encoded by nucleotides #427 to #1098 of SEQ ID NO:1 and #406 to #1098 of SEQ ID NO:3, respectively, and comprises the sequence of amino acids #1 to #224 of SEQ ID NO:2, or #1 to #231 of SEQ ID NO: 4, respectively.

It is expected that human BMP-17 and BMP-18 polypeptides, as expressed by mammalian cells such as CHO cells, exists as a heterogeneous population of active species of BMP-17 and BMP-18 proteins with varying N-termini. It is expected that active species will comprise an amino acid sequence beginning with the residue at amino acid #109 or #124 of SEQ ID NO:2 or #116 or #131 of SEQ ID NO: 4, respectively, or will comprise additional amino acid sequence further in the N-terminal direction. Thus, it is expected that DNA sequences encoding active BMP-17 and BMP-18 polypeptides will comprise a nucleotide sequence comprising nucleotides #1, #232, #406, #427, #751 or #796 to #1059 or #1098 of SEQ ID NO: 1, or #1, #232, #406, #427, #751 or #796 to #1059 or #1098 of SEQ ID NO: 3, respectively. Accordingly, active species of human BMP-17 and BMP-18 are expected to include those comprising amino acids #142, #−65, #−7, #1, #109 or #124 to #211 or #224 of SEQ ID NO:2, or #−135, #−58, #1, #8, #116 or #131 to #218 or #231 of SEQ ID NO:4, respectively.

A host cell may be transformed with a coding sequence encoding a propeptide suitable for the secretion of proteins by the host cell is linked in proper reading frame to the coding sequence for the mature BMP-17 and BMP-18 protein. For example, see U.S. Pat. No. 5,658,882, in which the propeptide of BMP-2 is fused to the DNA encoding a mature BMP-12 protein. The disclosure of this reference is hereby incorporated by reference. Thus, the present invention includes chimeric DNA molecules comprising a DNA sequence encoding a propeptide from a member of the TGF-β superfamily of proteins, other than BMP-17 and BMP-18, is linked in correct reading frame to a DNA sequence encoding human BMP-17 or BMP-18 protein, or a related protein. The term "chimeric" is used to signify that the propeptide originates from a different polypeptide than the native BMP-17 or BMP-18 protein.

The N-terminus of one active species of human BMP-17 is expected to be experimentally determined by expression in *E. coli* to be as follows: [M]ARVTV. Thus, it appears that the N-terminus of this species of BMP-17 is at amino acid #1 of SEQ ID NO: 1, and a DNA sequence encoding said species of BMP-17 would comprise nucleotides #427 to #1098 of SEQ ID NO: 1. The apparent molecular weight of human BMP-17 monomer is expected to be experimentally determined by SDS-PAGE to be approximately 24.8 kD on a Novex 16% tricine gel. The human BMP-17 protein is expected to exist as a clear, colorless solution in 0.1% trifluoroacetic acid.

It is expected that other BMP-17 proteins, as expressed by mammalian cells such as CHO cells, also exist as a heterogeneous population of active species of BMP-17-related protein with varying N-termini. For example, it is expected that active species of human BMP-17 protein will comprise an amino acid sequence beginning with the cysteine residue at amino acid #109 or the glutamic acid residue at position #124 of SEQ ID NO 2 or will comprise additional amino acid sequence further in the N-terminal direction. Thus, it is expected that DNA sequences encoding active BMP-17 proteins include those which comprise a nucleotide sequence comprising nucleotides #1, 232, 406, 427, 751 or 796 to #1059 or 1098 of SEQ ID NO: 1. Accordingly, active human BMP-17 proteins include those comprising amino acids #−142, −65, −7, 1, 109 or 124 to #211 or 224 of SEQ ID NO: 2.

The N-terminus of one active species of human BMP-18 is expected to be experimentally determined by expression in *E. coli* to be as follows: [M]LSPRS. Thus, it appears that the N-terminus of this species of BMP-18 is at amino acid #1 of SEQ ID NO: 3, and a DNA sequence encoding said species of BMP-18 would comprise nucleotides #406 to #1098 of SEQ ID NO:3. The apparent molecular weight of human BMP-18 monomer is expected to be experimentally determined by SDS-PAGE to be approximately 25.6 kD on a Novex 16% tricine gel. The human BMP-18 protein is expected to exist as a clear, colorless solution in 0.1% trifluoroacetic acid.

It is expected that other BMP-18 proteins, as expressed by mammalian cells such as CHO cells, also exist as a heterogeneous population of active species of BMP-18-related protein with varying N-termini. For example, it is expected that active species of human BMP-BMP-18 protein will comprise an amino acid sequence beginning with the cysteine residue at amino acid #116 or the glutamic acid residue at position #131 of SEQ ID NO:4 or will comprise additional amino acid sequence further in the N-terminal direction. Thus, it is expected that DNA sequences encoding active BMP-18 proteins include those which comprise a nucleotide sequence comprising nucleotides #1, 232, 406, 427, 751 or 796 to #1059 or 1098 of SEQ ID NO:3. Accordingly, active human BMP-18 proteins include those comprising amino acids #−135, −58, 1, 8, 116 or 131 to #218 or 231 of SEQ ID NO: 4.

The BMP-17 or BMP-18 proteins of the present invention, include polypeptides having a molecular weight of about 24.8 to 25.6 kD in monomeric form, said polypeptide comprising the amino acid sequence of SEQ ID NO: 2 or SEQ ID NO: 4, respectively, and having the ability to induce the formation of cartilage and/or bone and/or other connective tissue in the Rosen-Modified Sampath-Reddi ectopic implant assay, described in the examples.

The BMP-17 or BMP-18 proteins recovered from the culture medium are purified by isolating them from other proteinaceous materials from which they are co-produced and from other contaminants present. BMP-17 or BMP-18 proteins may be characterized by the ability to induce the formation of cartilage and/or bone and/or other connective tissue and other tissue repair and differentiation, for example, in the rat bone formation assay described below. In addition, BMP-17 or BMP-18 proteins may be further characterized by their effects upon the growth and/or differentiation of embryonic cells and/or stem cells. Thus, the proteins or compositions of the present invention may be characterized by the embryonic stem cell assay described below.

The BMP-17 or BMP-18 proteins provided herein also include factors encoded by the sequences similar to those of SEQ ID NO: 1 or SEQ ID NO: 3, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2 or SEQ ID NO: 4. These sequences, by virtue of sharing primary, secondary, or tertiary structural and conformational characteristics with bone growth factor polypeptides of SEQ ID NO: 2 or SEQ ID NO: 4 may possess biological properties in common therewith. It is know, for example that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C). Thus, these modifications and deletions of the native BMP-17 or BMP-18 may be employed as biologically active substitutes for naturally-occurring BMP-17 or BMP-18 and other polypeptides in therapeutic processes. It can be readily determined whether a given variant of BMP-17 or BMP-18 maintains the biological activity of BMP-17 or BMP-18 by subjecting both BMP-17 or BMP-18 and the variant of BMP-17 or BMP-18 to the assays described in the examples.

Other specific mutations of the sequences of BMP-17 or BMP-18 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of BMP-17 and BMP-18-related protein will also result in production of a non-glycosylated protein, even if the glycosylation sites are left unmodified.

The present invention also encompasses the novel DNA sequences, free of association with DNA sequences encoding other proteinaceous materials, and coding for expression of BMP-17 and BMP-18 proteins. These DNA sequences include those depicted in SEQ ID NO: 1 or SEQ ID NO: 3 in a 5' to 3' direction and those sequences which hybridize thereto under stringent hybridization washing conditions [for example, 0.1×SSC, 0.1% SDS at 65° C.; see, T. Maniatis et al, *Molecular Cloning (A Laboratory Manual)*, Cold Spring Harbor Laboratory (1982), pages 387 to 389] and encode a protein maintaining one or more of the activities disclosed herein for BMP-17 or BMP-18. These DNA sequences also include those which comprise the DNA sequence of SEQ ID NO: 1 or SEQ ID NO: 3 and those which hybridize thereto under stringent hybridization conditions and encode a protein which maintain the other activities disclosed for BMP-17 or BMP-18.

Similarly, DNA sequences which code for BMP-17 or BMP-18 polypeptides coded for by the sequences of SEQ ID NO: 1 or SEQ ID NO:3, respectively, or BMP-17 or BMP-18 polypeptides which comprise the amino acid sequence of SEQ ID NO: 2 or SEQ ID NO: 4, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 3 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-17 or BMP-18 polypeptides. The method of the present invention involves culturing a suitable cell line, which has been transformed with a DNA sequence encoding a BMP-17 or BMP-18 polypeptide of the invention, under the control of known regulatory sequences. The transformed host cells are cultured and the BMP-17 or BMP-18 polypeptides recovered and purified from the culture medium. The purified polypeptides are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7):1650 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of BMP-17 or BMP-18 is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-17 or BMP-18 polypeptides. Preferably the vectors contain the full novel DNA sequences described above which encode the novel factors of the invention. Additionally, the vectors contain appropriate expression control sequences permitting expression of the BMP-17 or BMP-18 polypeptide sequences. Alternatively, vectors incorporating modified sequences as described above are also embodiments of the present invention. Additionally, the sequence of SEQ ID NO: 1 or SEQ ID NO: 3 or other sequences encoding BMP-17 or BMP-18 polypeptides could be manipulated to express a mature BMP-17 or BMP-18 polypeptide by deleting BMP-17 or BMP-18 propeptide sequences and replacing them with sequences encoding the complete propeptides of other BMP proteins or members of the TGF-β superfamily. Thus, the present invention includes chimeric DNA molecules encoding a propeptide from a member of the TGF-β superfamily linked in correct reading frame to a DNA sequence encoding a BMP-17 or BMP-18 polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not forrn part of the present invention.

A protein of the present invention, which induces cartilage and/or bone and/or other connective tissue formation in circumstances where such tissue is not normally formed, has application in the healing of bone fractures and cartilage or other connective tissue defects in humans and other animals. Such a preparation employing a BMP-17 or BMP-18 polypeptide may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-17 or BMP-18-related polypeptide may be used in the treatment of periodontal disease, and in other tooth repair processes. Such agents may provide an environment to attract bone-forming cells, stimulate growth of bone-forming cells or induce differentiation of progenitors of bone-forming cells, and may also support the regeneration of the periodontal ligament and attachment apparatus, which connects bone and teeth. BMP-17 or BMP-18 polypeptides of the invention may also be useful in the treatment of osteoporosis. A variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, lung, epithelium, brain, spleen, cardiac, pancreas and kidney tissue. The proteins of the present invention may further be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

The proteins of the invention may also have other useful properties characteristic of the TGF-β superfamily of proteins. Such properties include angiogenic, chemotactic and/or chemoattractant properties, and effects on cells including induction of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formnation.

When dimerized as a homodimer or as a heterodimer with other BMPs, with other members of the TGF-β superfamily of proteins, or with inhibin-a proteins or inhibin-β proteins, the BMP-17 or BMP-18 heterodimer is expected to demonstrate effects on the production of follicle stimulating hormone (FSH), as described further herein. It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, BMP-17 or BMP-18 may be useful as a contraceptive based on the ability of inhibins to decrease fertility in female mammals and decrease spermatogenesis in male mammals. Administration of sufficient amounts of other inhibins can induce infertility in mammals. BMP-17 or BMP-18 may also be useful as a fertility inducing therapeutic, based upon the ability of activin molecules in stimulating FSH release from cells of the anterior pituitary. See, for example, U.S. Pat. No. 4,798,885. BMP-17 or BMP-18 may also be useful for advancement of the onset of fertility in sexually immature mammals, so as to increase the lifetime reproductive performance of domestic animals such as cows, sheep and pigs. It is further contemplated that BMP-17 or BMP-18 may be useful in modulating hematopoiesis by inducing the differentiation of erythroid cells [see, e.g., Broxmeyer et al, *Proc. Natl. Acad. Sci. USA*, 85:9052–9056 (1988) or Eto et al, *Biochem. Biophys. Res. Comm.*, 142:1095–1103 (1987)], for suppressing the development of gonadal tumors [see, e.g., Matzuk et al., *Nature*, 360:313–319 (1992)] or for augmenting the activity of bone morphogenetic proteins [see, e.g., Ogawa et al., *J. Biol. Chem.*, 267:14233–14237 (1992)].

BMP-17 and BMP-18 proteins may be further characterized by their ability to modulate the release of follicle stimulating hormone (FSH) in established in vitro bioassays using rat anterior pituitary cells as described [see, e.g., Vale et al, *Endocrinology*, 91:562–572 (1972); Ling et al., *Nature*, 321:779–782 (1986) or Vale et al., *Nature*, 321:776–779 (1986)]. It is contemplated that the BMP-17 or BMP-18 protein of the invention, when composed as a heterodimer with inhibin α or inhibin β chains, will exhibit regulatory effects, either stimulatory or inhibitory, on the release of follicle stimulating hormone (FSH), from anterior pituitary cells as described [Ling et al., *Nature*, 321:779–782 (1986) or Vale et al., *Nature*, 321:776–779 (1986); Vale et al, *Endocrinology*, 91:562–572 (1972). Therefore, depending on the particular composition, it is expected that the BMP-17 or BMP-18 protein of the invention may have contrasting and opposite effects on the release of follicle stimulating hormone (FSH) from the anterior pituitary.

Activin A (the homodimeric composition of inhibin $β_A$) has been shown to have erythropoietic-stimulating activity [see e.g. Eto et al., *Biochem. Biophys. Res. Commun.*, 142:1095–1103 (1987) and Murata et al., *Proc. Natl. Acad. Sci. U.S.A.*, 85:2434–2438 (1988) and Yu et al., Nature, 330:765–767 (1987)]. It is contemplated that the BMP-17 and -18 proteins of the invention may have a similar erythropoietic-stimulating activity. This activity of the BMP-17 and BMP-18 proteins may be further characterized by the ability of the BMP-17 and BMP-18 proteins to demonstrate erythropoietin activity in the biological assay performed using the human K-562 cell line as described by [Lozzio et al., *Blood*, 45:321–334 (1975) and U.S. Pat. No. 5,071,834].

A further aspect of the invention is a therapeutic method and composition for repairing fractures and other conditions related to cartilage and/or bone and/or other connective tissue defects or periodontal diseases. The invention further comprises therapeutic methods and compositions for wound healing and tissue repair. Such compositions comprise a therapeutically effective amount of at least one of the BMP-17 or BMP-18-related proteins of the invention in admixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in U.S. Pat. No. 5,661,007; BMP-10, disclosed in U.S. Pat. No. 5,637,480; BMP-11, disclosed in U.S. Pat. No. 5,639,638; BMP-12 or BMP-13, disclosed in U.S. Pat. No. 5,658,882; or BMP-15, disclosed in U.S. Pat. No. 5,635,372; or BMP-16, disclosed in co-pending U.S. patent application Ser. No. 08/715,202. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein.

It is expected that human BMP-17 and BMP-18 protein may exist in nature as monomers, or as homodimers or heterodimers. To promote the formation of dimers of BMP-17 or BMP-18 and useful proteins with increased stability, one can genetically engineer the DNA sequence of SEQ ID NO:1 or SEQ ID NO: 3 to provide one or more additional cysteine residues to increase potential dimer formation. The resulting DNA sequence would be capable of producing a "cysteine added variant" of BMP-17 or BMP-18. In a preferred embodiment, one would engineer the DNA sequence of SEQ ID NO: 1 or SEQ ID NO: 3 so that one or more codons may be altered to a nucleotide triplet encoding a cysteine residue, such as TGT or TGC. Alternatively, one can produce "cysteine added variants" of BMP-17 or BMP-18 protein by altering the sequence of the protein at the amino acid level by altering one or more amino acid residues of SEQ ID NO:2 or SEQ ID NO: 4 to cysteine. Production of "cysteine added variants" of proteins is described in U.S. Pat. No. 5,166,322, the disclosure of which is hereby incorporated by reference. In preferred embodiments, the glutamic acid residue at position #173 of SEQ. ID NO: 2 or position #180 of SEQ. ID NO: 4 is replaced by a cysteine residue.

It is expected that the proteins of the invention may act in concert with or perhaps synergistically with other related proteins and growth factors. Further therapeutic methods and compositions of the invention therefore comprise a therapeutic amount of at least one BMP-17 or BMP-18 protein of the invention with a therapeutic amount of at least one other member of the TGF-β superfamily of proteins, such as the BMP proteins disclosed in the applications described above. Such combinations may comprise separate molecules of the BMP proteins or heteromolecules comprised of different BMP moieties. For example, a method and composition of the invention may comprise a disulfide linked dimer comprising a BMP-17 or BMP-18 protein subunit and a subunit from one of the "BMP" proteins described above. Thus, the present invention includes a purified BMP-17 or BMP-1 8-related polypeptide which is a heterodimer wherein one subunit comprises the amino acid sequence from amino acid #1 to amino acid #224 of SEQ ID NO:2 or #1 to #231 of SEQ ID NO:4, and one subunit comprises an amino acid sequence for a bone morphogenetic protein selected from the group consisting of BMP-2, BMP-3, BMP-4, BMP-5, BMP-6, BMP-7, BMP-8, BMP-9, BMP-10, BMP-11, BMP-12, BMP-13, BMP-15, or BMP-16. A further embodiment may comprise a heterodimer of BMP-17 or BMP-18-related moieties, for example a heterodimer of human BMP-17 and human BMP-18 or of human BMP-17 and the murine Lefty protein, which is a homologue of human BMP-17 and BMP-18. Further, BMP-17 or BMP-18 protein may be combined with other agents beneficial to the treatment of the bone and/or cartilage and/or other connective tissue defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), parathyroid hormone related peptide (PTHrP), leukemia inhibitory factor (LIB/HILA/DA), insulin-like growth factors (IGF-I and IGF-II). Portions of these agents may also be used in compositions of the present invention. The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with the BMP-17 or BMP-18 proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or other connective tissue or other tissue damage. Topical administration may be suitable for wound healing and tissue repair. Therapeutically useful agents other than the BMP-17 or BMP-18 proteins which may also optionally be included in the composition as described above, may alternatively or additionally, be administered simultaneously or sequentially with the BMP composition in the methods of the invention.

Preferably for bone and/or cartilage and/or other connective tissue formation, the composition includes a matrix capable of delivering BMP-17 or BMP-18-related or other BMP proteins to the site of bone and/or cartilage and/or other connective tissue damage, providing a structure for the developing bone and cartilage and other connective tissue and optimally capable of being resorbed into the body. The matrix may provide slow release of BMP-17 or BMP-18 protein and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the BMP-17 or BMP-18 compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-17 or BMP-18 protein, e.g. amount of bone or other tissue weight desired to be formed, the site of bone or tissue damage, the condition of the damaged bone tissue, the size of a wound, type of damaged tissue, the patient's age, sex, and diet, the severity of any infection, time of administration and other clinical factors. The dosage may vary with the type of matrix used in the reconstitution and the types of BMP proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also effect the dosage.

Progress can be monitored by periodic assessment of bone or tissue growth and/or repair. The progress can be monitored, for example, x-rays, histomorphometric determinations and tetracycline labeling.

The following examples illustrate practice of the present invention with respect to human BMP-17 and human BMP-18 and other BMP-17 and BMP-18-related proteins. The skilled artisan will recognize that numerous variations and modifications are possible. These variations and modifications constitute part of the present invention.

EXAMPLES

Example 1

Isolation of DNA

DNA sequences encoding human BMP-17 and BMP-18 and human BMP-17 and BMP-18-related proteins may be isolated by various techniques known to those skilled in the art using the sequence information provided in the Sequence Listings.

Based on the knowledge of BMP proteins and other proteins within the TGF-β family, it is predicted that the carboxyl-terminal portion of these molecules (mature peptide) would exhibit greater sequence conservation than the more amino-terminal portions (propeptide region). This sequence relationship between BMP proteins and other proteins within the TGF-β family enables those skilled in the art to design DNA probes from the carboxyl-terminal encoding portion (mature peptide encoding region) of these molecules which can be utilized to identify related BMP proteins and other proteins within the TGF-β family. The mature peptide encoding region of the murine lefty gene may be utilized to identify human BMP-17 and BMP-18 and related proteins.

The bacteriophage AF02, which contains the DNA sequence encoding human BMP-17 has been deposited with the American Type Culture Collection, 10801 university Boulevard, Manassas, Va. 20110-2209 ATTC under the accession #202060 on Nov. 24, 1997. This deposit meets the requirements of the Budapest Treaty of the International Recognition of the Deposit of Microorganisms for the Purpose of Patent Procedure and Regulations thereunder.

The bacteriophage AF04, which contains the DNA sequence encoding human BMP-18 has been deposited with the American Type Culture Collection, 10801 university Boulevard, Manassas, Va. 20110-2209 ATTC under the accession #202059 on Nov. 24, 1997. This deposit meets the requirements of the Budapest Treaty of the International Recognition of the Deposit of Microorganisms for the Purpose of Patent Procedure and Regulations thereunder.

Based on the knowledge of other BMP proteins and other proteins within the TGF-β family, it is predicted that the human BMP-17 and BMP-18 precursor polypeptides would be cleaved at the multibasic sequence in agreement with a proposed consensus proteolytic processing sequence of Arg-X-X-Arg corresponding to amino acids-4to -1 of SEQ ID NO:1. Cleavage of the human BMP-17 precursor polypeptide is expected to generate a 224 amino acid mature peptide beginning with the amino acid alanine at position #1 of SEQ ID NO:2, or a 101 amino acid mature peptide beginning with the amino acid glutamic acid at position #124 of SEQ ID NO: 2. Cleavage of the human BMP-18 precursor polypeptide is expected to generate a 231 amino acid mature peptide beginning with the amino acid leucine at position #1 of SEQ ID NO:4, or a 101 amino acid mature peptide beginning with the amino acid glutamic acid at position #131 of SEQ ID NO: 4. The processing of human BMP-17 or BMP-18 into the mature forms is expected to potentially involve dimerization and removal of the N-terminal region in a manner analogous to the processing of the related protein TGF-β [Gentry et al., *Molec & Cell. Biol.*, 8:4162 (1988); Derynck et al. *Nature*, 316:701 (1985)].

It is contemplated therefore that the mature active species of human BMP-17 and BMP-18 may comprise homodimers of two polypeptide subunits, each subunit comprising amino acids #1 to #224 of SEQ ID NO:2 or # 1 to #231 of SEQ ID NO:4, respectively, with a predicted molecular weight of approximately 49 to 52 kD. Further active species are contemplated comprising at least amino acids #109 to #211 of SEQ ID NO:2 or #116 to #218 of SEQ ID NO: 4, thereby including the first and last conserved cysteine residues. As with other members of the TGF-β/BMP family of proteins, the carboxyl-terminal portion of the human BMP-17 and BMP-18 polypeptides exhibit greater sequence conservation than the more amino-terminal portion.

The human BMP-17 (SEQ ID NO:1) or BMP-18 DNA sequence (SEQ ID NO:3), or a portion thereof, can be used as a probe to identify a human cell line or tissue which synthesizes human BMP-17 or BMP-18 or a human BMP-17 or BMP-18-related mRNA. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from the coding sequence of human BMP-17 and BMP-18.

Alternatively, the human BMP-17 or BMP-18 sequence may be used to design oligonucleotide primers which will specifically amplify a portion of the human BMP-17 or BMP-18 or related encoding sequences. It is contemplated that these human BMP-17 and human BMP-18 derived primers would allow one to specifically amplify corresponding human BMP-17 or BMP-18 or related encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other λ bacteriophage vectors known to those skilled in the art, for example, λZAP by established techniques (Toole et al., supra). It is also possible to perform the oligonucleotide primer directed amplification reaction, described above, directly on a preestablished human cDNA or genomic library which has been cloned into a λ bacteriophage vector. In such cases, a library which yields a specifically amplified DNA product encoding a portion of the human BMP-17 or BMP-18 or related protein could be screened directly, utilizing the fragment of amplified human BMP-17, BMP-18 or related encoding DNA as a probe.

Additional methods known to those skilled in the art may be used to isolate other full-length cDNAs encoding human BMP-17 or BMP-18 or related proteins, or full length cDNA clones encoding BMP-17 or BMP-18 or related proteins of the invention from species other than humans, particularly other mammalian species.

Example 2

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)].

Specifically, W-20 cells are a clonal bone marrow stromal cell line derived from adult mice by researchers in the laboratory of Dr. D. Nathan, Children's Hospital, Boston, MA. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 Units/ml penicillin +100 μg/ml streptomycin. The cells are allowed to attach overnight in a 95% air, 5% $CO_2$ incubator at 37° C. The 200 μl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 μl per well of calcium/magnesium free phosphate buffered saline and these washes are discarded. 50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 μl of 0.2 N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
| --- | --- |
| 0.000 | 0 |
| 0.006 | 0.261 +/- .024 |
| 0.012 | 0.521 +/- .031 |
| 0.018 | 0.797 +/- .063 |
| 0.024 | 1.074 +/- .061 |
| 0.030 | 1.305 +/- .083 |

Absorbance values for known amounts of BMPs can be determnined and converted to pmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
| --- | --- | --- |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-17 and BMP-18 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutaniine and the test substance in a total volume of 2 ml. Each test substance is administered to triplicate wells. The test substances are incubated with the W-20 cells for a total of 96 hours with replacement at 48 hours by the same test medias. At the end of 96 hours, 50 μl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
| --- | --- |
| 0 | 0.8 |
| 2 | 0.9 |
| 4 | 0.8 |
| 8 | 2.2 |
| 17 | 2.7 |
| 31 | 3.2 |
| 62 | 5.1 |
| 125 | 6.5 |
| 250 | 8.2 |
| 500 | 9.4 |
| 1000 | 10.0 |

Example 3

ROSEN MODIFIED SAMPATH-REDDI ASSAY

A modified version of the rat bone formnation assay described in Sampath and Reddi, *Proc. Natl. Acad. Sci. USA*, 80:6591–6595 (1983) is used to evaluate bone and/or cartilage and/or other connective tissue activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatese analysis [see, Reddi et al, *Proc. Natl. Acad. Sci.*, 69:1601 (1972)].

The other half of each implant is fixed and processed for histological analysis. 1 μm glycolmethacrylate sections are stained with Von Kossa and acid fuschin to score the amount of induced bone and cartilage and other connective tissue formation present in each implant. the terms +1 through +5 represent the area of each histological section of an implant occupied by new bone and/or cartilage cells and matrix. A score of +5 indicates that greater than 50% of the implant is new and/or cartilage produced as a direct result of protein in the implant.

A score of +4, +3, +2, and +1 would indicate that greater than 40%, 30%, 20% and 10 respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, Histology (JB Lippincott Co. (1979), pp. 367–369, the disclosure of which is hereby incorporated by reference]. These findings may be reproduced in additional assays in which tendon/ligament-like tissues are observed in the BMP-17 and BMP-18-related protein containing implants. The BMP-17 and BMP-18-related proteins of this invention may be assessed for activity on this assay.

Example 4
Expression of BMP-17 and BMP-18

In order to produce murine, human or other mammalian BMP-17 and BMP-18 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-17 and BMP-18 is contemplated to be stably transformed mammalian cells.

One skilled in the art can construct mammalian expression vectors by employing the sequence of SEQ ID NO: 1 or SEQ ID NO: 3, or other DNA sequences encoding BMP-17 and BMP-18 or related proteins or other modified sequences and known vectors, such as pCD [Okayamaet al., *Mol. Cell Biol.*, 2:161 (1982)], pJL3, pJL4 [Gough et al., *EMBO J.*, 4:645–653 (1985)] and pMT2 CXM. The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection, 10801 university Boulevard, Manassas, Va. 20110-2209 under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' (SEQ. ID. NO:5)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

(SEQ ID NO:6)
5'-CTGCAGGCGAGCCTGAATTCCTCGAGCCATCATG-3'
   PstI          Eco RIXhoI

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECAT1 [S. K. Jung, et al, *J. Virol* 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

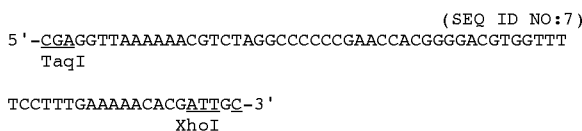

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRi-TaqI fragment, and the 68 bp oligonucleotide adapter TaqI-16hoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-17 and BMP-18-related DNA sequences. For instance, BMP-17 and BMP-18 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-17 and BMP-18-related proteins. Additionally, the sequence of SEQ ID NO:1, SEQ ID NO: 3 or other sequences encoding BMP-17 and BMP-1 8-related proteins can be manipulated to express a mature BMP-17 or BMP-18 or related protein by deleting BMP-17 or BMP-18 encoding propeptide sequences and replacing them with sequences encoding the complete propeptides of other BMP proteins.

One skilled in the art can manipulate the sequences of SEQ ID NO: I or SEQ ID NO: 3 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-17 or BMP-18-related coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a BMP-17 and BMP-18-related protein expressed thereby. For a strategy for producing extracellular expression of BMP-17 or BMP-18-related proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-17 or BMP-18 or related protein of the invention in mammalian cells may involve the construction of cells containing multiple copies of the heterologous BMP-17 or BMP-18 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a BMP-17 or BMP-18 or related protein of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5uM MTX) as described in Kaufman et al., *Mol Cell Biol.*, 5:1650 (1983). Transformants are cloned, and biologically active BMP-17 or BMP-18 expression is monitored by the Rosen-modified Sampath-Reddi rat bone formation assay described above in Example 3. BMP-17 and BMP-18 protein expression should increase with increasing levels of MTX resistance. BMP-17 and BMP-18 polypeptides are characterized using standard techniques known in the art such as pulse labeling with [35S] methionine or cysteine and polyacrylamide gel electrophoresis. Similar procedures can be followed to produce other related BMP-17 and BMP-18 or related proteins.

Example 5

Biological Activity of Expressed BMP-17 and BMP-18

To measure the biological activity of the expressed BMP-17 and BMP-18 or related proteins obtained in Example 4 above, the proteins are recovered from the cell culture and purified by isolating the BMP-17, BMP-18 or related proteins from other proteinaceous materials with which they are co-produced as well as from other contaminants. The purified protein may be assayed in accordance with the rat bone formation assay described in Example 3.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

Example 6

Using Northern analysis, BMP-17, BMP-18 and related proteins can be tested for their effects on various cell lines. Suitable cell lines include cell lines derived from E13 mouse limb buds. After 10 days of treatment with BMP-17, BMP-18 or related protein, the cell phenotype is examined histologically for indications of tissue differentiation. In addition, Northern analysis of mRNA from BMP-17, BMP-18 or related protein treated cells can be performed for various markers including one or more of the following markers for bone, cartilage and/or tendon/ligament, as described in Table IV:

TABLE IV

| Marker | Bone | Cartilage | Tendon/Ligament |
| --- | --- | --- | --- |
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1] - Marker seen early, marker not seen as mature bone tissue forms
[2] - Marker depends upon site of tendon; strongest at bone interface
[3] - Marker seen at low levels Example 7
Embryonic Stem Cell Assay In order to assay the effects of the BMP-17 and BMP-18 proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3a an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA molecule comprising a DNA sequence selected from the group consisting of:
   (a) nucleotides #1, 232, 406, 427, 751 or 796 to #1059 or 1098 of SEQ ID NO:1;
   (b) nucleotides encoding amino acids #-142, -65, -7, 1, 109 or 124 to #211 or 224 SEQ ID NO:2
   (c) nucleotides #1, 232, 406, 427, 751 or 796 to #1059 or 1098 of SEQ ID NO:3;
   (d) nucleotides encoding amino acids #-135, -58, 1, 8, 116 or 131 to #218 or 231 of SEQ ID NO:4; and
   (e) equivalent degenerative codon sequences of (a), (b), (c) or (d).

2. A host cell transformed with the DNA sequence of claim 1.

3. A vector comprising a DNA molecule of claim 1 in operative association with an expression control sequence therefor.

4. A host cell transformed with the vector of claim 3.

5. An isolated DNA molecule comprising a DNA sequence consisting of nucleotides #427 to #1098 of SEQ ID NO:1.

6. An isolated DNA molecule comprising a DNA sequence consisting of nucleotides #406 to #1098 of SEQ ID NO:3.

7. A vector comprising a DNA molecule of claim 5 in operative association with an expression control sequence therefor.

8. A host cell transformed with the vector of claim 7.

9. A vector comprising a DNA molecule of claim 6 in operative association with an expression control sequence therefor.

10. A host cell transformed with the vector of claim 9.

11. A method for producing a purified human bone morphogenetic protein-17 (BMP) or BMP-18 protein, said method comprising the steps of:

(a) culturing a host cell transformed with a DNA molecule according to claim 1; and
   (b) recovering and purifying said human BMP-17 or BMP-18 protein from the culture medium.

12. The method of claim 11, wherein said host cell is transformed with a DNA molecule comprising a DNA coding sequence consisting of nucleotide #427 to #1098 of SEQ ID NO: 1.

13. The method of claim 12, wherein said host cell is a mammalian cell and the DNA molecule further comprises a DNA sequence encoding a propeptide from a member of the TGF-β superfamily of proteins, said DNA sequence encoding a propeptide being linked in proper reading frame to the DNA coding sequence.

14. The method of claim 11, wherein said host cell is transformed with a DNA molecule comprising a DNA coding sequence consisting of nucleotide #406 to #1098 of SEQ ID NO: 3.

15. The method of claim 14, wherein said host cell is a mammalian cell and the DNA molecule further comprises a DNA sequence encoding a propeptide from a member of the TGF-β superfamily of proteins, said DNA sequence encoding a propeptide being linked in proper reading frame to the DNA coding sequence.

16. A chimeric DNA molecule comprising a DNA sequence encoding a propeptide from a member of the TGF-β superfamily of proteins linked in frame to a DNA sequence encoding a bone morphogenetic protein-17 polypeptide, said BMP-17 polypeptide comprising amino acid #1 to #224 of SEQ ID NO: 2.

17. A chimeric DNA molecule comprising a DNA sequence encoding a propeptide from a member of the TGF-β superfamily of proteins linked in frame to a DNA sequence encoding a bone morphogenetic protein-18 polypeptide, said BMP-18 polypeptide comprising amino acid #1 to #231 of SEQ ID NO: 4.

\* \* \* \* \*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
          (A) LENGTH: 1101 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: pro_peptide
          (B) LOCATION: 1..426

(ix) FEATURE:
          (A) NAME/KEY: mat_peptide
          (B) LOCATION: 427..1098

(ix) FEATURE:
          (A) NAME/KEY: CDS
          (B) LOCATION: 1..1098

(xi) SEQUENCE DESCRIPTION: SEQ ID NO:1:

```
ATG CAG CCC CTG TGG CTC TGC TGG GCA CTC TGG GTG TTG CCC CTG GCC      48
Met Gln Pro Leu Trp Leu Cys Trp Ala Leu Trp Val Leu Pro Leu Ala
-142     -140              -135              -130

AGC CCC GGG GCC GCC CTG ACC GGG GAG CAG CTC CTG GGC AGC CTG CTG      96
Ser Pro Gly Ala Ala Leu Thr Gly Glu Gln Leu Leu Gly Ser Leu Leu
        -125              -120              -115

CGG CAG CTG CAG CTC AAA GAG GTG CCC ACC CTG GAC AGG GCC GAC ATG     144
Arg Gln Leu Gln Leu Lys Glu Val Pro Thr Leu Asp Arg Ala Asp Met
-110              -105              -100              -95
```

```
GAG GAG CTG GTC ATC CCC ACC CAC GTG AGG GCC CAG TAC GTG GCC CTG         192
Glu Glu Leu Val Ile Pro Thr His Val Arg Ala Gln Tyr Val Ala Leu
            -90             -85             -80

CTG CAG CGC AGC CAC GGG GAC CGC TCC CGC GGA AAG AGG TTC AGC CAG         240
Leu Gln Arg Ser His Gly Asp Arg Ser Arg Gly Lys Arg Phe Ser Gln
        -75             -70             -65

AGC TTC CGA GAG GTG GCC GGC AGG TTC CTG GCG TTG GAG GCC AGC ACA         288
Ser Phe Arg Glu Val Ala Gly Arg Phe Leu Ala Leu Glu Ala Ser Thr
    -60             -55             -50

CAC CTG CTG GTG TTC GGC ATG GAG CAG CGG CTG CCG CCC AAC AGC GAG         336
His Leu Leu Val Phe Gly Met Glu Gln Arg Leu Pro Pro Asn Ser Glu
    -45             -40             -35

CTG GTG CAG GCC GTG CTG CGG CTC TTC CAG GAG CCG GTC CCC AAG GCC         384
Leu Val Gln Ala Val Leu Arg Leu Phe Gln Glu Pro Val Pro Lys Ala
-30             -25             -20             -15

GCG CTG CAC AGG CAC GGG CGG CTG TCC CCG CGC AGC GCC CGG GCC CGG         432
Ala Leu His Arg His Gly Arg Leu Ser Pro Arg Ser Ala Arg Ala Arg
            -10             -5              1

GTG ACC GTC GAG TGG CTG CGC GTC CGC GAC GAC GGC TCC AAC CGC ACC         480
Val Thr Val Glu Trp Leu Arg Val Arg Asp Asp Gly Ser Asn Arg Thr
         5              10              15

TCC CTC ATC GAC TCC AGG CTG GTG TCC GTC CAC GAG AGC GGC TGG AAG         528
Ser Leu Ile Asp Ser Arg Leu Val Ser Val His Glu Ser Gly Trp Lys
     20              25              30

GCC TTC GAC GTG ACC GAG GCC GTG AAC TTC TGG CAG CAG CTG AGC CGG         576
Ala Phe Asp Val Thr Glu Ala Val Asn Phe Trp Gln Gln Leu Ser Arg
 35              40              45              50

CCC CGG CAG CCG CTG CTG CTA CAG GTG TCG GTG CAG AGG GAG CAT CTG         624
Pro Arg Gln Pro Leu Leu Leu Gln Val Ser Val Gln Arg Glu His Leu
             55              60              65

GGC CCG CTG GCG TCC GGC GCC CAC AAG CTG GTC CGC TTT GCC TCG CAG         672
Gly Pro Leu Ala Ser Gly Ala His Lys Leu Val Arg Phe Ala Ser Gln
         70              75              80

GGG GCG CCA GCC GGG CTT GGG GAG CCC CAG CTG GAG CTG CAC ACC CTG         720
Gly Ala Pro Ala Gly Leu Gly Glu Pro Gln Leu Glu Leu His Thr Leu
     85              90              95

GAC CTT GGG GAC TAT GGA GCT CAG GGC GAC TGT GAC CCT GAA GCA CCA         768
Asp Leu Gly Asp Tyr Gly Ala Gln Gly Asp Cys Asp Pro Glu Ala Pro
100             105             110

ATG ACC GAG GGC ACC CGC TGC TGC CGC CAG GAG ATG TAC ATT GAC CTG         816
Met Thr Glu Gly Thr Arg Cys Cys Arg Gln Glu Met Tyr Ile Asp Leu
115             120             125             130

CAG GGG ATG AAG TGG GCC GAG AAC TGG GTG CTG GAG CCC CCG GGC TTC         864
Gln Gly Met Lys Trp Ala Glu Asn Trp Val Leu Glu Pro Pro Gly Phe
             135             140             145

CTG GCT TAT GAG TGT GTG GGC ACC TGC CGG CAG CCC CCG GAG GCC CTG         912
Leu Ala Tyr Glu Cys Val Gly Thr Cys Arg Gln Pro Pro Glu Ala Leu
         150             155             160

GCC TTC AAG TGG CCG TTT CTG GGG CCT CGA CAG TGC ATC GCC TCG GAG         960
Ala Phe Lys Trp Pro Phe Leu Gly Pro Arg Gln Cys Ile Ala Ser Glu
     165             170             175

ACT GCC TCG CTG CCC ATG ATC GTC AGC ATC AAG GAG GGA GGC AGG ACC        1008
Thr Ala Ser Leu Pro Met Ile Val Ser Ile Lys Glu Gly Gly Arg Thr
180             185             190

AGG CCC CAG GTG GTC AGC CTG CCC AAC ATG AGG GTG CAG AAG TGC AGC        1056
Arg Pro Gln Val Val Ser Leu Pro Asn Met Arg Val Gln Lys Cys Ser
195             200             205             210

TGT GCC TCG GAT GGT GCG CTC GTG CCA AGG AGG CTC CAG CCA                1098
Cys Ala Ser Asp Gly Ala Leu Val Pro Arg Arg Leu Gln Pro
```

TAG                                                                1101

(2) INFORMATION FOR SEQ ID NO:2:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Pro Leu Trp Leu Cys Trp Ala Leu Trp Val Leu Pro Leu Ala
-142        -140                -135                -130

Ser Pro Gly Ala Ala Leu Thr Gly Glu Gln Leu Leu Gly Ser Leu Leu
    -125            -120                -115

Arg Gln Leu Gln Leu Lys Glu Val Pro Thr Leu Asp Arg Ala Asp Met
-110            -105                -100                    -95

Glu Glu Leu Val Ile Pro Thr His Val Arg Ala Gln Tyr Val Ala Leu
                -90          -85                    -80

Leu Gln Arg Ser His Gly Asp Arg Ser Arg Gly Lys Arg Phe Ser Gln
        -75              -70                    -65

Ser Phe Arg Glu Val Ala Gly Arg Phe Leu Ala Leu Glu Ala Ser Thr
        -60              -55                -50

His Leu Leu Val Phe Gly Met Glu Gln Arg Leu Pro Pro Asn Ser Glu
        -45              -40              -35

Leu Val Gln Ala Val Leu Arg Leu Phe Gln Glu Pro Val Pro Lys Ala
-30              -25              -20                      -15

Ala Leu His Arg His Gly Arg Leu Ser Pro Arg Ser Ala Arg Ala Arg
                -10              -5                        1

Val Thr Val Glu Trp Leu Arg Val Arg Asp Asp Gly Ser Asn Arg Thr
         5              10                  15

Ser Leu Ile Asp Ser Arg Leu Val Ser Val His Glu Ser Gly Trp Lys
     20              25                  30

Ala Phe Asp Val Thr Glu Ala Val Asn Phe Trp Gln Gln Leu Ser Arg
 35              40                  45                      50

Pro Arg Gln Pro Leu Leu Leu Gln Val Ser Val Gln Arg Glu His Leu
             55                  60                      65

Gly Pro Leu Ala Ser Gly Ala His Lys Leu Val Arg Phe Ala Ser Gln
             70                  75                  80

Gly Ala Pro Ala Gly Leu Gly Glu Pro Gln Leu Glu Leu His Thr Leu
         85              90                  95

Asp Leu Gly Asp Tyr Gly Ala Gln Gly Asp Cys Asp Pro Glu Ala Pro
     100             105                 110

Met Thr Glu Gly Thr Arg Cys Cys Arg Gln Glu Met Tyr Ile Asp Leu
115             120                 125                     130

Gln Gly Met Lys Trp Ala Glu Asn Trp Val Leu Glu Pro Pro Gly Phe
             135                 140                 145

Leu Ala Tyr Glu Cys Val Gly Thr Cys Arg Gln Pro Pro Glu Ala Leu
             150                 155                 160

Ala Phe Lys Trp Pro Phe Leu Gly Pro Arg Gln Cys Ile Ala Ser Glu
             165                 170                 175

Thr Ala Ser Leu Pro Met Ile Val Ser Ile Lys Glu Gly Gly Arg Thr
             180                 185                 190
```

```
Arg Pro Gln Val Val Ser Leu Pro Asn Met Arg Val Gln Lys Cys Ser
195                 200                 205                 210

Cys Ala Ser Asp Gly Ala Leu Val Pro Arg Arg Leu Gln Pro
                215                 220
```

(2) INFORMATION FOR SEQ ID NO:3:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: pro_peptide
        (B) LOCATION: 1..405

(ix) FEATURE:
        (A) NAME/KEY: mat_peptide
        (B) LOCATION: 406..1098

(ix) FEATURE:
        (A) NAME/KEY: CDS
        (B) LOCATION: 1..1098

(xi) SEQUENCE DESCRIPTION: SEQ ID NO:3:

```
ATG TGG CCC CTG TGG CTC TGC TGG GCA CTC TGG GTG CTG CCC CTG GCT       48
Met Trp Pro Leu Trp Leu Cys Trp Ala Leu Trp Val Leu Pro Leu Ala
-135                -130                -125                -120

GGC CCC GGG GCG GCC CTG ACC GAG GAG CAG CTC CTG GGC AGC CTG CTG       96
Gly Pro Gly Ala Ala Leu Thr Glu Glu Gln Leu Leu Gly Ser Leu Leu
                -115                -110                -105

CGG CAG CTG CAG CTC AGC GAG GTG CCC GTA CTG GAC AGG GCC GAC ATG      144
Arg Gln Leu Gln Leu Ser Glu Val Pro Val Leu Asp Arg Ala Asp Met
            -100                 -95                 -90

GAG AAG CTG GTC ATC CCC GCC CAC GTG AGG GCC CAG TAT GTA GTC CTG      192
Glu Lys Leu Val Ile Pro Ala His Val Arg Ala Gln Tyr Val Val Leu
         -85                 -80                 -75

CTG CGG CGC AGC CAC GGG GAC CGC TCC CGC GGA AAG AGG TTC AGC CAG      240
Leu Arg Arg Ser His Gly Asp Arg Ser Arg Gly Lys Arg Phe Ser Gln
     -70                 -65                 -60

AGC TTC CGA GAG GTG GCC GGC AGG TTC CTG GCG TCG GAG GCC AGC ACA      288
Ser Phe Arg Glu Val Ala Gly Arg Phe Leu Ala Ser Glu Ala Ser Thr
-55                 -50                 -45                 -40

CAC CTG CTG GTG TTC GGC ATG GAG CAG CGG CTG CCG CCC AAC AGC GAG      336
His Leu Leu Val Phe Gly Met Glu Gln Arg Leu Pro Pro Asn Ser Glu
                 -35                 -30                 -25

CTG GTG CAG GCC GTG CTG CGG CTC TTC CAG GAG CCG GTC CCC AAG GCC      384
Leu Val Gln Ala Val Leu Arg Leu Phe Gln Glu Pro Val Pro Lys Ala
            -20                 -15                 -10

GCG CTG CAC AGG CAC GGG CGG CTG TCC CCG CGC AGC GCC CAG GCC CGG      432
Ala Leu His Arg His Gly Arg Leu Ser Pro Arg Ser Ala Gln Ala Arg
         -5                   1                   5

GTG ACC GTC GAG TGG CTG CGC GTC CGC GAC GAC GGC TCC AAC CGC ACC      480
Val Thr Val Glu Trp Leu Arg Val Arg Asp Asp Gly Ser Asn Arg Thr
 10                  15                  20                  25

TCC CTC ATC GAC TCC AGG CTG GTG TCC GTC CAC GAG AGC GGC TGG AAG      528
Ser Leu Ile Asp Ser Arg Leu Val Ser Val His Glu Ser Gly Trp Lys
                 30                  35                  40

GCC TTC GAC GTG ACC GAG GCC GTG AAC TTC TGG CAG CAG CTG AGC CGG      576
Ala Phe Asp Val Thr Glu Ala Val Asn Phe Trp Gln Gln Leu Ser Arg
             45                  50                  55
```

```
CCC CGG CAG CCG CTG CTG CTA CAG GTG TCG GTG CAG AGG GAG CAT CTG        624
Pro Arg Gln Pro Leu Leu Leu Gln Val Ser Val Gln Arg Glu His Leu
            60                  65                  70

GGC CCG CTG GCG TCC GGC GCC CAC AAG CTG GTC CGC TTT GCC TCG CAG        672
Gly Pro Leu Ala Ser Gly Ala His Lys Leu Val Arg Phe Ala Ser Gln
        75                  80                  85

GGG GCG CCA GCC GGG CTT GGG GAG CCC CAG CTG GAG CTG CAC ACC CTG        720
Gly Ala Pro Ala Gly Leu Gly Glu Pro Gln Leu Glu Leu His Thr Leu
 90                  95                 100                 105

GAC CTC AGG GAC TAT GGA GCT CAG GGC GAC TGT GAC CCT GAA GCA CCA        768
Asp Leu Arg Asp Tyr Gly Ala Gln Gly Asp Cys Asp Pro Glu Ala Pro
                110                 115                 120

ATG ACC GAG GGC ACC CGC TGC TGC CGC CAG GAG ATG TAC ATT GAC CTG        816
Met Thr Glu Gly Thr Arg Cys Cys Arg Gln Glu Met Tyr Ile Asp Leu
                    125                 130                 135

CAG GGG ATG AAG TGG GCC AAG AAC TGG GTG CTG GAG CCC CCG GGC TTC        864
Gln Gly Met Lys Trp Ala Lys Asn Trp Val Leu Glu Pro Pro Gly Phe
            140                 145                 150

CTG GCT TAC GAG TGT GTG GGC ACC TGC CAG CAG CCC CCG GAG GCC CTG        912
Leu Ala Tyr Glu Cys Val Gly Thr Cys Gln Gln Pro Pro Glu Ala Leu
        155                 160                 165

GCC TTC AAT TGG CCA TTT CTG GGG CCG CGA CAG TGT ATC GCC TCG GAG        960
Ala Phe Asn Trp Pro Phe Leu Gly Pro Arg Gln Cys Ile Ala Ser Glu
170                 175                 180                 185

ACT GCC TCG CTG CCC ATG ATC GTC AGC ATC AAG GAG GGA GGC AGG ACC       1008
Thr Ala Ser Leu Pro Met Ile Val Ser Ile Lys Glu Gly Gly Arg Thr
                190                 195                 200

AGG CCC CAG GTG GTC AGC CTG CCC AAC ATG AGG GTG CAG AAG TGC AGC       1056
Arg Pro Gln Val Val Ser Leu Pro Asn Met Arg Val Gln Lys Cys Ser
                    205                 210                 215

TGT GCC TCG GAT GGG GCG CTC GTG CCA AGG AGG CTC CAG CCA               1098
Cys Ala Ser Asp Gly Ala Leu Val Pro Arg Arg Leu Gln Pro
            220                 225                 230

TAG                                                                   1101

(2) INFORMATION FOR SEQ ID NO:4:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:4:

Met Trp Pro Leu Trp Leu Cys Trp Ala Leu Trp Val Leu Pro Leu Ala
-135                -130                -125                -120

Gly Pro Gly Ala Ala Leu Thr Glu Glu Gln Leu Leu Gly Ser Leu Leu
                -115                -110                -105

Arg Gln Leu Gln Leu Ser Glu Val Pro Val Leu Asp Arg Ala Asp Met
                -100                 -95                 -90

Glu Lys Leu Val Ile Pro Ala His Val Arg Ala Gln Tyr Val Val Leu
            -85                  -80                  -75

Leu Arg Arg Ser His Gly Asp Arg Ser Arg Gly Lys Arg Phe Ser Gln
        -70                  -65                  -60

Ser Phe Arg Glu Val Ala Gly Arg Phe Leu Ala Ser Glu Ala Ser Thr
-55                  -50                  -45                  -40

His Leu Leu Val Phe Gly Met Glu Gln Arg Leu Pro Pro Asn Ser Glu
                 -35                  -30                  -25
```

-continued

```
Leu Val Gln Ala Val Leu Arg Leu Phe Gln Glu Pro Val Pro Lys Ala
        -20                 -15                 -10

Ala Leu His Arg His Gly Arg Leu Ser Pro Arg Ser Ala Gln Ala Arg
         -5                  1                  5

Val Thr Val Glu Trp Leu Arg Val Arg Asp Asp Gly Ser Asn Arg Thr
 10              15                  20                      25

Ser Leu Ile Asp Ser Arg Leu Val Ser Val His Glu Ser Gly Trp Lys
             30                  35                      40

Ala Phe Asp Val Thr Glu Ala Val Asn Phe Trp Gln Gln Leu Ser Arg
             45                  50                      55

Pro Arg Gln Pro Leu Leu Gln Val Ser Val Gln Arg Glu His Leu
         60              65                  70

Gly Pro Leu Ala Ser Gly Ala His Lys Leu Val Arg Phe Ala Ser Gln
 75              80                  85

Gly Ala Pro Ala Gly Leu Gly Glu Pro Gln Leu Glu Leu His Thr Leu
 90              95                 100                     105

Asp Leu Arg Asp Tyr Gly Ala Gln Gly Asp Cys Asp Pro Glu Ala Pro
            110                 115                     120

Met Thr Glu Gly Thr Arg Cys Cys Arg Gln Glu Met Tyr Ile Asp Leu
            125                 130                     135

Gln Gly Met Lys Trp Ala Lys Asn Trp Val Leu Glu Pro Pro Gly Phe
            140                 145                 150

Leu Ala Tyr Glu Cys Val Gly Thr Cys Gln Gln Pro Pro Glu Ala Leu
            155                 160                 165

Ala Phe Asn Trp Pro Phe Leu Gly Pro Arg Gln Cys Ile Ala Ser Glu
170             175                 180                     185

Thr Ala Ser Leu Pro Met Ile Val Ser Ile Lys Glu Gly Gly Arg Thr
            190                 195                     200

Arg Pro Gln Val Val Ser Leu Pro Asn Met Arg Val Gln Lys Cys Ser
            205                 210                 215

Cys Ala Ser Asp Gly Ala Leu Val Pro Arg Arg Leu Gln Pro
            220             225                 230
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CATGGGCAGC TCGAG        15

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGCAGGCGA GCCTGAATTC CTCGAGCCAT CATG        34

-continued (2) INFORMATION FOR SEQ ID NO:7:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CGAGGTTAAA AAACGTCTAG GCCCCCCGAA CCACGGGGAC GTGGTTTTCC TTTGAAAAAC        60
ACGATTGC                                                                 68
```